United States Patent
Frontanes et al.

(10) Patent No.: US 6,399,101 B1
(45) Date of Patent: Jun. 4, 2002

(54) STABLE THYROID HORMONE PREPARATIONS AND METHOD OF MAKING SAME

(75) Inventors: Ramon A. Frontanes, Caguas; Maria S. Bruno, Guaynabo; Hector L. Garcia, Cidra, all of PR (US); Pahala Simamora, Cardova, TN (US); Maria A. Perez, Aguas Buenas, PR (US)

(73) Assignee: Mova Pharmaceutical Corp., Caguas, PR (US)

( * ) Notice: Subject to any disclaimer, the term of this patent is extended or adjusted under 35 U.S.C. 154(b) by 0 days.

(21) Appl. No.: 09/538,461

(22) Filed: Mar. 30, 2000

(51) Int. Cl.⁷ .............................. A61K 9/20; A61P 5/14
(52) U.S. Cl. ..................... 424/488; 424/464; 424/465; 514/960
(58) Field of Search ................................ 424/488, 464, 424/465; 514/960

(56) References Cited

U.S. PATENT DOCUMENTS

| | | |
|---|---|---|
| 4,415,547 A | 11/1983 | Yu et al. |
| 4,666,703 A | 5/1987 | Kopf |
| 4,910,023 A | 3/1990 | Botzolakis et al. |
| 5,004,613 A | 4/1991 | Radebaugh et al. |
| 5,032,405 A | 7/1991 | Huang et al. |
| 5,073,380 A | 12/1991 | Babu et al. |
| 5,200,193 A | 4/1993 | Radebaugh et al. |
| 5,202,128 A | 4/1993 | Morella et al. |
| 5,225,202 A | 7/1993 | Hodges et al. |
| 5,225,204 A | 7/1993 | Chen et al. |
| 5,330,766 A | 7/1994 | Morella et al. |
| 5,378,474 A | 1/1995 | Morella et al. |
| 5,462,747 A | 10/1995 | Radebaugh et al. |
| 5,490,990 A | 2/1996 | Grabowski et al. |
| 5,536,507 A | 7/1996 | Abramowitz et al. |
| 5,543,155 A | 8/1996 | Fekete et al. |
| 5,585,115 A | 12/1996 | Sherwood et al. |
| 5,635,209 A | 6/1997 | Groenewoud et al. |
| 5,681,583 A | 10/1997 | Conte et al. |
| 5,725,883 A | 3/1998 | Staniforth et al. |
| 5,725,884 A | 3/1998 | Sherwood et al. |
| 5,741,524 A | 4/1998 | Staniforth et al. |
| 5,747,068 A | 5/1998 | Mendizabal |
| 5,753,254 A | 5/1998 | Khan et al. |
| 5,780,057 A | 7/1998 | Conte et al. |
| 5,800,834 A | 9/1998 | Spireas et al. |
| 5,858,412 A | 1/1999 | Staniforth et al. |
| 5,866,166 A | 2/1999 | Staniforth et al. |
| 5,895,663 A | 4/1999 | Irwin et al. |
| 5,948,438 A | 9/1999 | Staniforth et al. |
| 5,955,105 A | 9/1999 | Mitra et al. |
| 6,190,696 B1 * | 2/2001 | Groenewoud ............... 424/464 |

FOREIGN PATENT DOCUMENTS

WO 99/15155 4/1999

OTHER PUBLICATIONS

Allen, J. D., et al., "Improving DC with SMCC", *Manufacturing Chemist*, 19–23, Dec. 1996.

Brownley, Jr., C. A., et al., "Browning of Spray–Processed Lactose", *J. of Pharm. of Sci.*, 53 (4): 452–454, 1964.

(List continued on next page.)

*Primary Examiner*—Edward J. Webman
*Assistant Examiner*—Helen Nguyen
(74) *Attorney, Agent, or Firm*—Burns, Doane, Swecker & Mathis, L.L.P.

(57) ABSTRACT

Provided is a pharmaceutical preparation of thyroid hormone and a process of making a tablet formulation of the pharmaceutical preparation using direct compression. In a preferred embodiment, the pharmaceutical preparation comprises levothyroxine sodium and silicified microcrystalline cellulose.

15 Claims, 16 Drawing Sheets

OTHER PUBLICATIONS

Castello, R. A., et al., "Discoloration of Tablets Containing Amines and Lactose", *J. of Pharm. Sci.*, 51 (2): 106–108, 1962.

Debord, B., et al., "Study of Different Crystalline Forms of Mannitol: Comparative Behaviour Under Compression", *Drug Devel. and Ind. Pharm.*, 13 (9–11): 1533–1546, 1987.

Duvall, R. N., et al., "Comparison of Reactivity of Amphetamine, Methamphetamine, and Dimethylamphetamine with Lactose and Related Compounds", *J. of Pharm Sci.*, 54 (4): 607–611, 1965.

Edge, S., et al., "The Location of silicon dioxide in silicified Microcrystalline Cellulose", *Pharm. Pharmacol. Commun.*, 3: 371–376, 1999.

Gupta, V. D., et al., "Effect of Excipients on the Stability of Levothyroxine Sodium Tablets", *J. of Clinical Pharm. Ther.*, 15: 331–336, 1990.

Kanig, J. L., "Properties of Fused Mannitol in Compressed Tablets", *J. of Pharm. Sci.*, 53 (2): 188–192, 1964.

Riba, X. S., et al., "Silicified Microcrystalline Cellulose: A Comparative Evaluation of This New high Functionality Direct Compression Excipient", *Pharm. Res.*, 4 (11): S–11, #1038, 1997.

Richheimer, S. L., et al., "Determination of Liothyronine and Levothyroxine in Thyroid Preparations by Liquid Chromatography", *J. of Pharm. Sci.*, 2 (75): 215–217, 1986.

Sheskey, P. J., et al., "Investigation Into The Mechanical Behavior of Selected Pharmaceutical Polymer Excipients as Binding Agents in Roller Compaction", *Pharm. Res.*, 14 (11): S–417, #2624, 1997.

Sherwood, B. E., et al., "A New Class of High–Functionality Excipients: Silicified Microcrystalline Cellulose", *Pharm. Tech.*, 22 (10): 78–88, 1998.

Tobyn, M. J., et al., "Physicochemical Comparison Between Microcrystalline Cellulose and Silicified Microcrystalline Cellulose", *Inter. J. of Pharm.*, 169: 183–194, 1998.

Ward, D. R., et al., "Dissolution and Compatibility Considerations for the Use of Mannitol in Solid Dosage Forms", *J. of Pharm. Sci.*, 58 (12): 1464–1467, 1969.

Won, C. M., "Kinetics of Degradation of Levothyroxine in Aqueous Solution and in Solid State", *Pharm Res.*, 9 (1): 131–137, 1992.

Wirth, D. D., et al., "Maillard Reaction of Lactose and Fluoxetine Hydrochloride, a Secondary Amine", *J. of Pham. Sci.*, 87 (1); 31–39, 1998.

* cited by examiner

STABLE THYROID HORMONE PREPARATIONS AND METHOD OF MAKING SAME

BACKGROUND OF THE INVENTION

1. Field of the Invention

The present invention is directed to therapeutic agents for the treatment of hormone disorders and the method for preparing those agents. More specifically, the present invention relates to stable pharmaceutical preparations containing thyroxine drugs, especially levothyroxine sodium, which is the sodium salt of the levo isomer of thyroxine. L-thyroxine is the principal hormone secreted by the normal thyroid gland. The thyroid gland is stimulated to secrete thyroid hormones by the action of thyroid stimulating hormone (TSH), which is produced in the anterior pituitary gland. TSH secretion is then controlled by thyrotropin-releasing hormone (TRH), produced in the hypothalamus. Thyroid hormones circulating in the blood act as feedback inhibitors of both TSH and TRH secretion.

Thyroxine may be obtained from the thyroid gland of domesticated animals, or alternatively, the hormone can be prepared synthetically. Levothyroxine and other thyroid hormones are known to serve as specific replacement therapy when the thyroid function has been reduced or is completely absent for a variety of disease states, including, for instance, myxedema, cretinism and obesity. Levothyroxine is also indicated as a pituitary TSH suppressant in the treatment or prevention of euthyroid goiters.

2. Brief Description of Related Art

Pharmaceutical preparations containing levothyroxine hormone are known to exhibit deficiencies with regard to uniformity, stability and shelf life. More specifically, levothyroxine sodium hormone is hygroscopic and degrades rapidly under conditions of high humidity or in the presence of other moisture sources or light and under conditions of high temperature. Moreover, levothyroxine is known to degrade in the presence of certain pharmaceutical excipients such as carbohydrates, including lactose, sucrose, dextrose and starch, as well as certain dyes.

Commercial preparations currently marketed include Levothroid®, Levoxyl®, Synthroid® and Levo-T®. These products, which include lactose as the major component of the excipient matrix, exhibit poor characteristics with regard to stability and uniformity. As noted in the *Handbook of Pharmaceutical Excipients*, Second Edition, p. 257, a Maillard-type condensation reaction is likely to occur between lactose and compounds with a primary amine group to form brown-colored products. Accordingly, it has been found that lactose reacts with levothyroxine resulting in degradation of the drug. It is believed that the amino group of the L-tyrosine portion of the levothyroxine molecule reacts with the glycosidic hydroxyl group of the glucose unit of the lactose excipient, undergoing the Maillard reaction. This degradation of levothyroxine results in decreased stability for the drug formulation. There is, then, a need in the art for a levothyroxine formulation which does not utilize lactose or other excipients which can react with the levothyroxine and lead to degradation of the drug.

A few attempts have been made to prepare thyroxine formulations without the excipients of the commercial products described above. U.S. Pat. No. 5,225,204, issued to Chen et al, describes a dosage formulation complex of hydrated levothyroxine sodium which includes Poloxamer or polyvinylpyrrolidone and is granulated with a polar organic solvent before being uniformly adsorbed on a cellulose compound. Other embodiments of the '204 patent describe a levothyroxine sodium formulation prepared with the use of an organic solvent or in a dry state by mixing levothyroxine sodium with a cellulose complexing agent and subsequently combining this mixture with a cellulose carrier. No data on the stability of these formulations was provided.

U.S. Pat. No. 5,955,105, issued to Knoll Pharmaceutical Company, describes thyroid hormone preparations stabilized by an inorganic salt, a carbohydrate having a molecular weight of greater than 500, or glycine. Suitable carbohydrate binders include microcrystalline cellulose, maltodextrin, starch and hydroxypropyl cellulose having a molecular weight between 80,000 and 1,150,000. Preferred embodiments of the invention were prepared in the substantial absence of lactose, glucose, sucrose, polyvinylpyrrolidone, and/or a Poloxamer. According to the '105 patent, the levothyroxine formulations of U.S. Pat. No. 5,225,204 did not provide suitable stability. Example 1 involved the use of PVP and example 2 involved dry mixing levothyroxine sodium with hydroxypropyl cellulose with subsequent combination of this mixture with a microcrystalline cellulose carrier. These examples of the '204 patent were repeated by the applicants of the '105 patent and the formulations were subjected to stability tests. The results of these tests are provided in the '105 patent.

U.S. Pat. No. 5,635,209, issued to Vintage Pharmaceuticals, Inc., is directed to a stabilized composition of levothyroxine sodium medication containing potassium iodide and a microcrystalline cellulose. This formulation may also include a disintegrant, a lubricant and a dye. The composition of the '209 patent is undesirable since it includes the extra ingredient potassium iodide, which distorts the results of a determination of the stability of the levothyroxine sodium.

U.S. Pat. No. 5,753,254, issued to Knoll Aktiengesellschaft, relates to a solid fast dispersing dosage form wherein the therapeutic agents containing thyroid hormones have a formulation including the hormone, a disintegrating agent, a flavoring agent and a lubricating agent. The disintegrating agent may be starch, agar, bentonite, cellulose, microcrystalline cellulose, methylcellulose, carmellose, croscarmellose sodium, alginic acid, guar gum, silicon dioxide and sodium lauryl sulphate. The flavoring agent may be a sweetening agent, a peppermint oil and/or fruit flavor, a flavor enhancing agent or an ingredient which induces the formation of saliva, such as an organic acid like citric and malic acid. The lubricating agent may be magnesium stearate, calcium stearate, stearic acid and mixtures thereof. Optional ingredients may also be present. This formulation is intended to be fast dissolving and stability issues are not discussed.

Each of these patents attempts to remedy the deficiencies of the commercial levothyroxine products by using various excipients besides the standard lactose. Microcrystalline cellulose (MCC) is widely used as a filler and binder for pharmaceutical formulations prepared by both wet granulation and direct compression processes. However, as set forth in the '105 patent, the combination of levothyroxine and microcrystalline cellulose as disclosed in the '204 patent did not provide adequate stability. Moreover, microcrystalline cellulose used in direct compression tableting has a number of limitations, such as low bulk density, high lubricant sensitivity, poor flow characteristics and the influence of moisture on the compression characteristics.

Thus, there is still a need in the art for a stable, uniform formulation of levothyroxine which can be readily formed into dosage forms and which is substantially free of the disadvantages, defects and limitations of the formulations disclosed in the art.

An object of the present invention is to provide a stable thyroid hormone preparation which can be readily formed into a dosage formulation. A further object of this invention is to provide a stabilized preparation of a thyroid hormone which resists degradation by light, heat, humidity or association with commonly used excipients. Another object of the present invention is to provide a novel pharmaceutical preparation and a manufacturing process therefor to improve the product performance of levothyroxine sodium tablets in terms of uniformity, stability and shelf life.

A further object of the invention is to provide a pharmaceutical preparation in which an excipient provides a matrix to capture and protect levothyroxine sodium in order to stabilize the preparation. Another object of the present invention is to provide a process for the manufacture of stabilized levothyroxine tablets using direct compression.

SUMMARY OF THE INVENTION

In accordance with the foregoing objectives, there is provided by the present invention a stabilized pharmaceutical preparation comprising a therapeutically effective amount of a thyroid hormone and silicified microcrystalline cellulose.

In a more preferred embodiment, the thyroid hormone is levothyroxine sodium. The thyroid hormone preparations of the present invention provide a stabilizing matrix consisting essentially of silicified microcrystalline cellulose which captures and protects a therapeutically effective amount of levothyroxine sodium particles within the stabilizing matrix.

In a further embodiment, the present invention is directed to a direct compression method for the manufacture of a pharmaceutical tablet preparation comprising the steps of: (a) forming an active blend by blending in intimate admixture silicified microcrystalline cellulose and a therapeutic agent comprising one or more thyroid hormone or hormones; (b) forming a color blend by blending in intimate admixture one or more pharmaceutically acceptable dyes and silicified microcrystalline cellulose; (c) combining the active blend, the color blend and a disintegrant in a preblend; (d) adding a lubricant to the preblend to form final blend; and (e) compressing the final blend to form a pharmaceutical tablet preparation.

DETAILED DESCRIPTION OF THE INVENTION

Figure 1A:
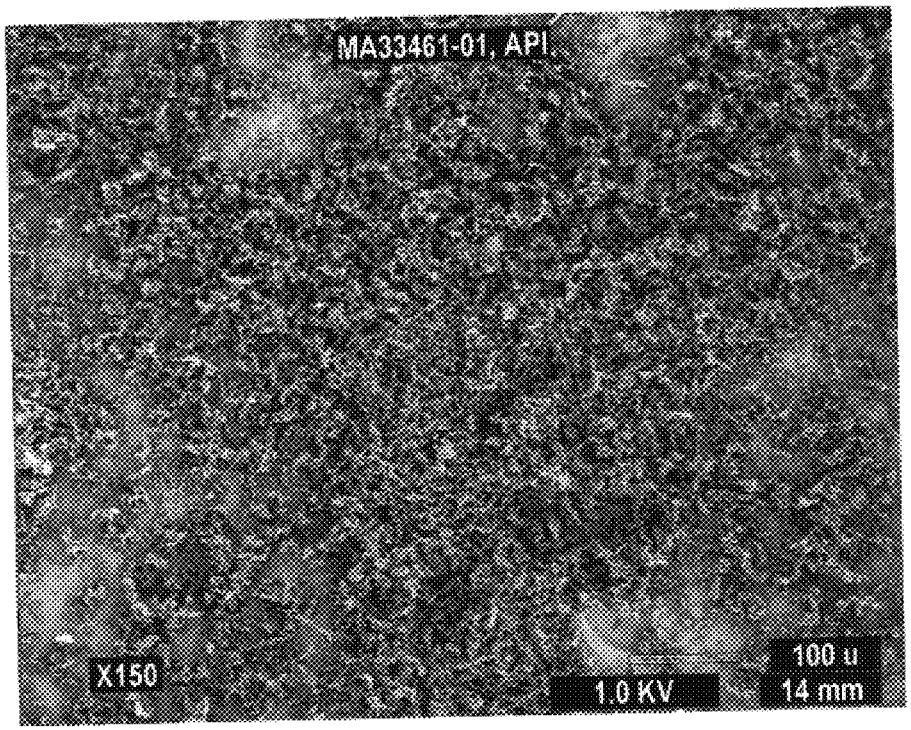
FIGS. 1A thru 1D are scanning electron microscopy (SEM) micrographs showing the smooth crystalline structure of levothyroxine particles.
Figure 1B:
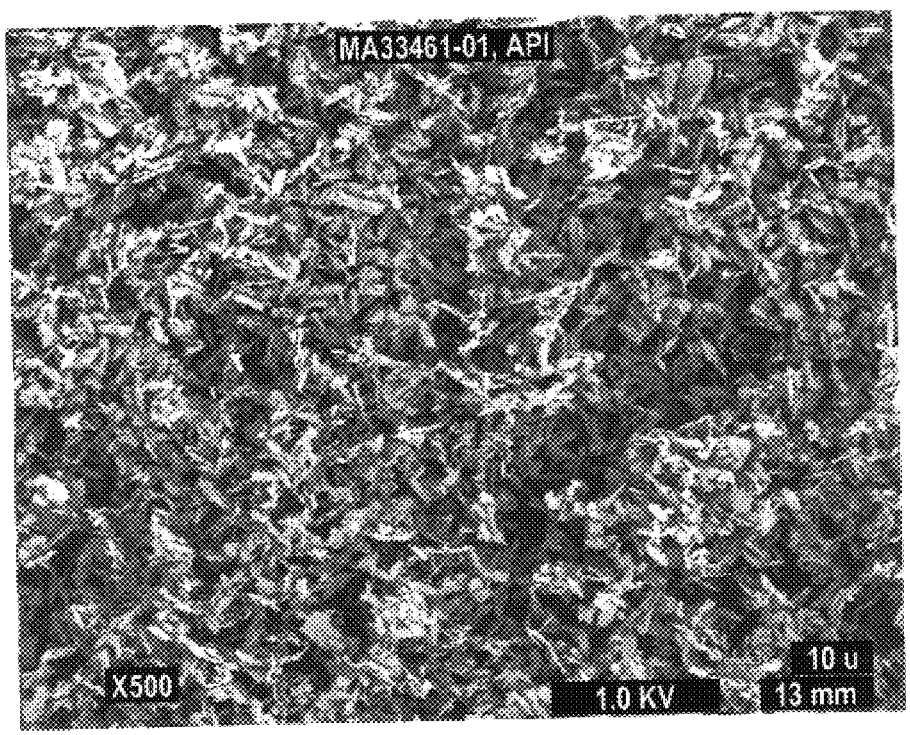
Figure 1C:
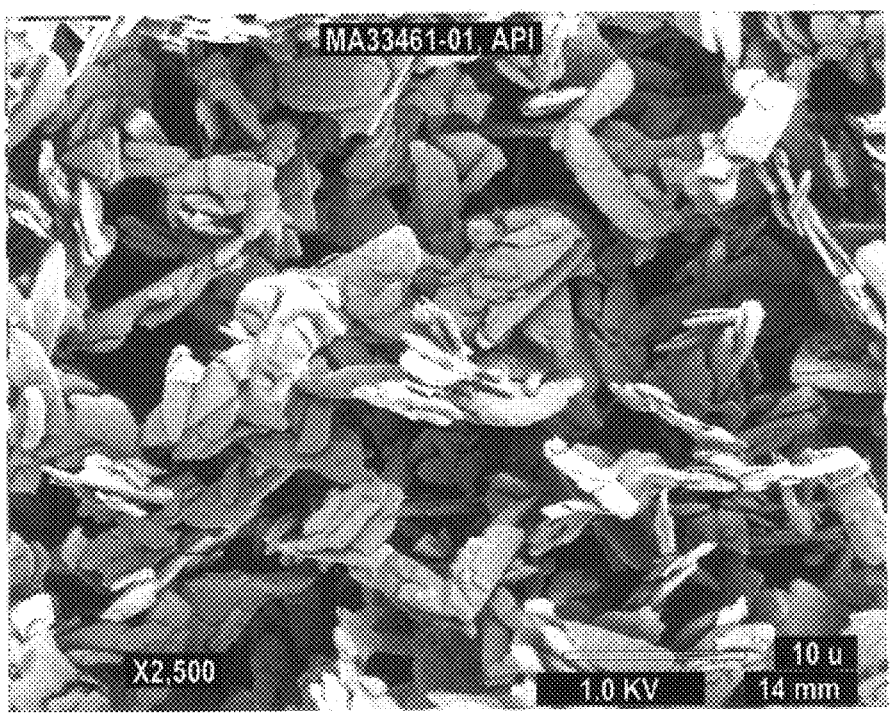
Figure 1D:
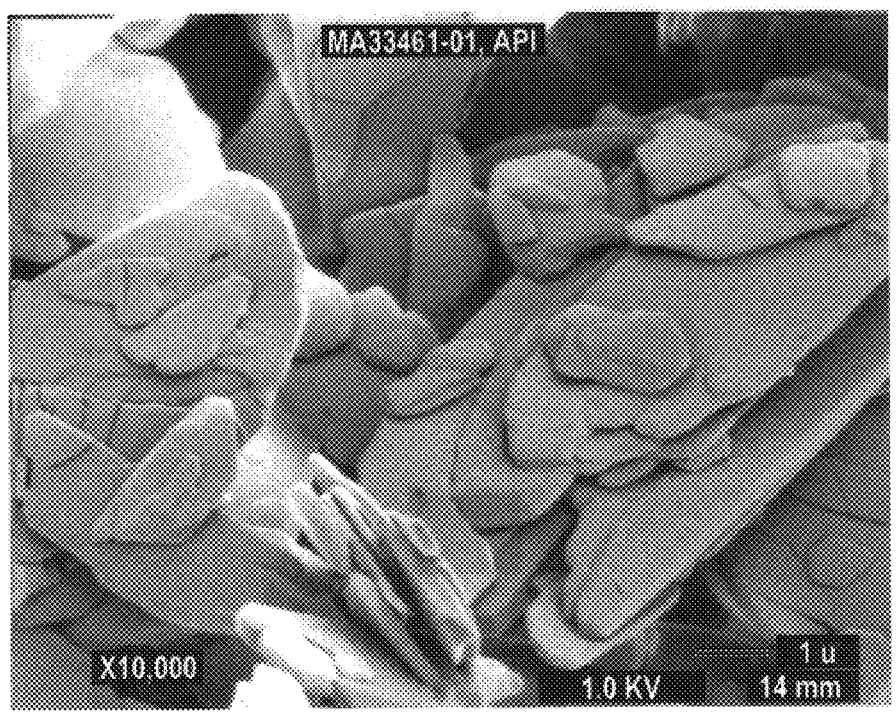
Figure 2A:
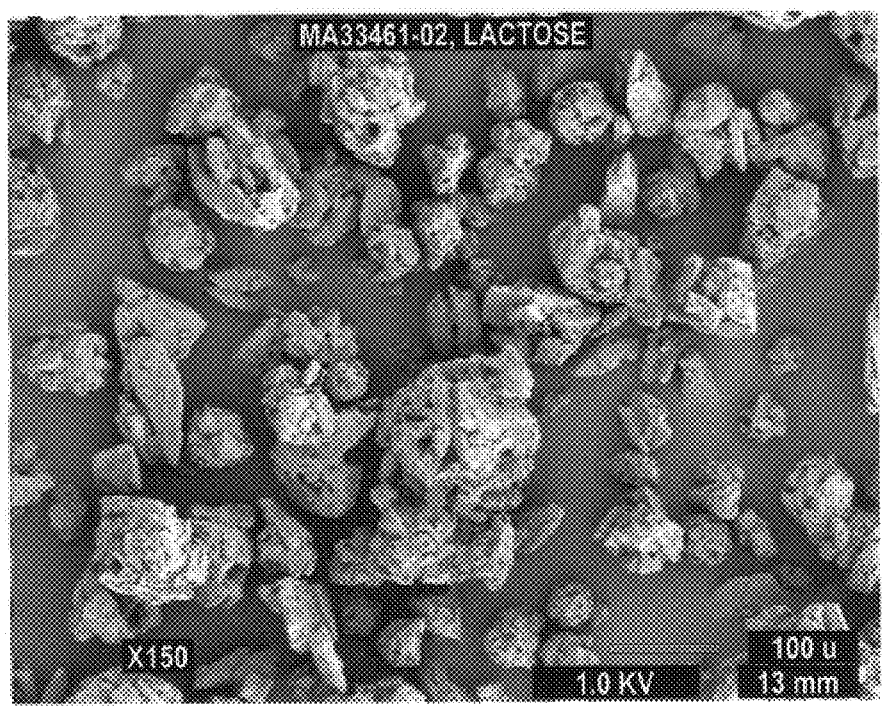
FIGS. 2A thru 2D are SEM micrographs showing the structure of a direct mixture of amorphous and crystalline grade lactose.
Figure 2B:
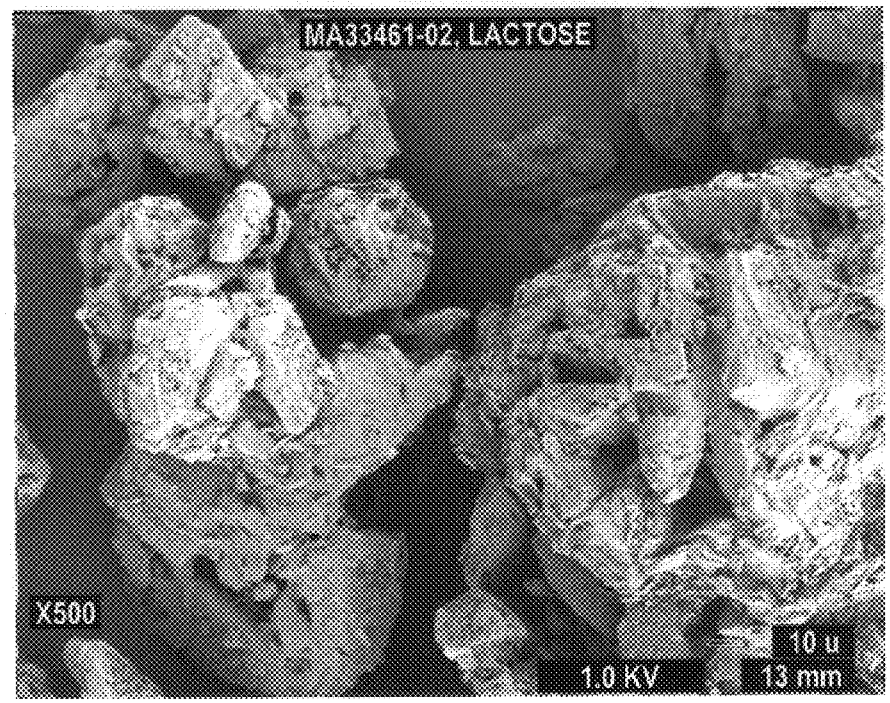
Figure 2C:
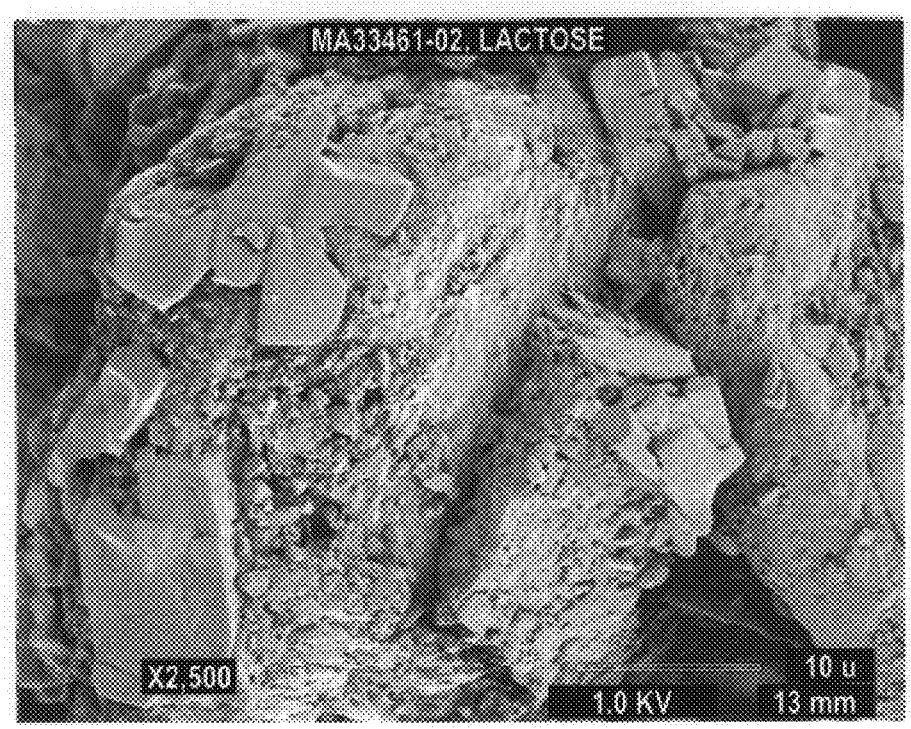
Figure 2D:
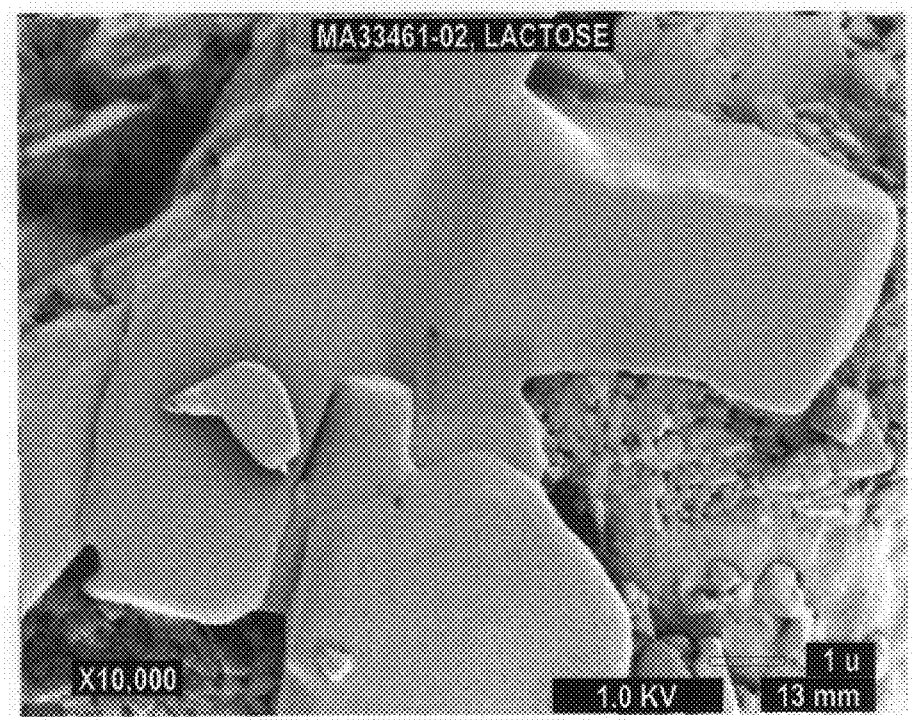
Figure 3A:
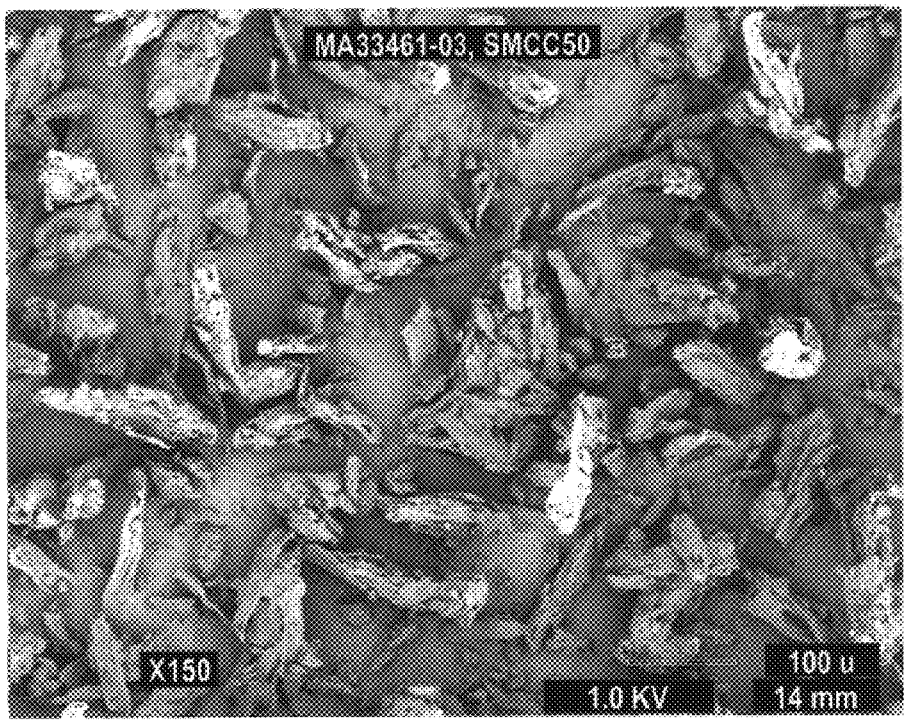
FIGS. 3A thru 3D are SEM micrographs showing the structure of silicified microcrystalline cellulose (Prosolv®50).
Figure 3B:
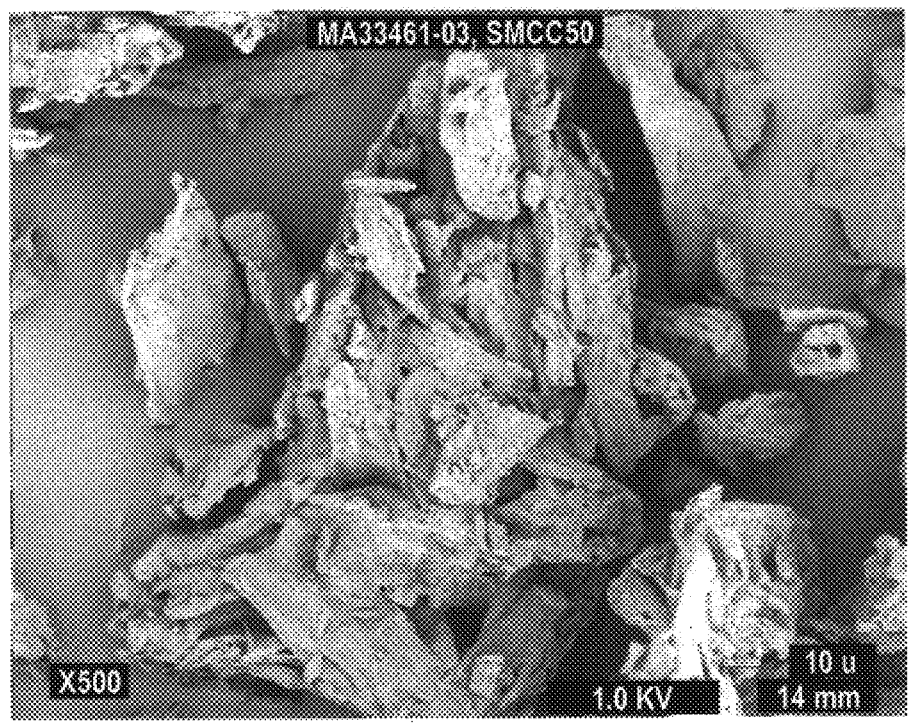
Figure 3C:
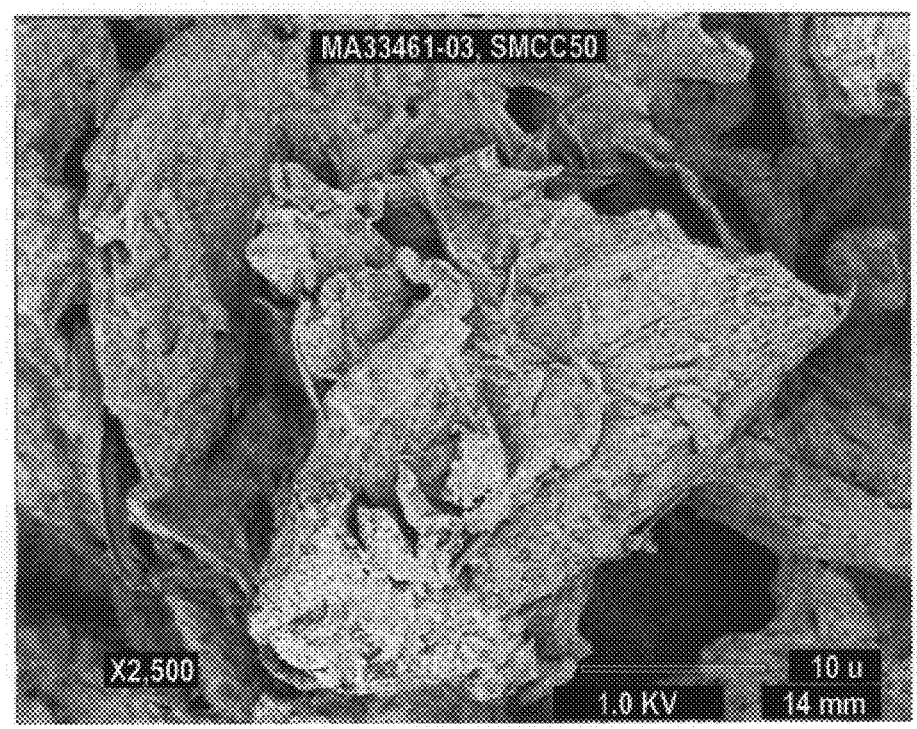
Figure 3D:
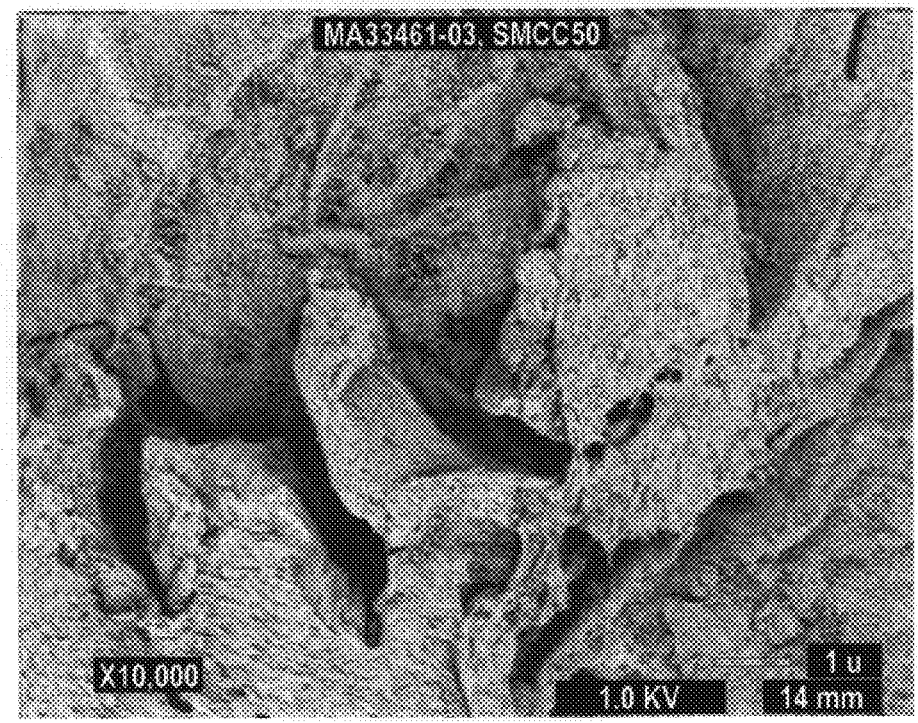
Figure 4A:
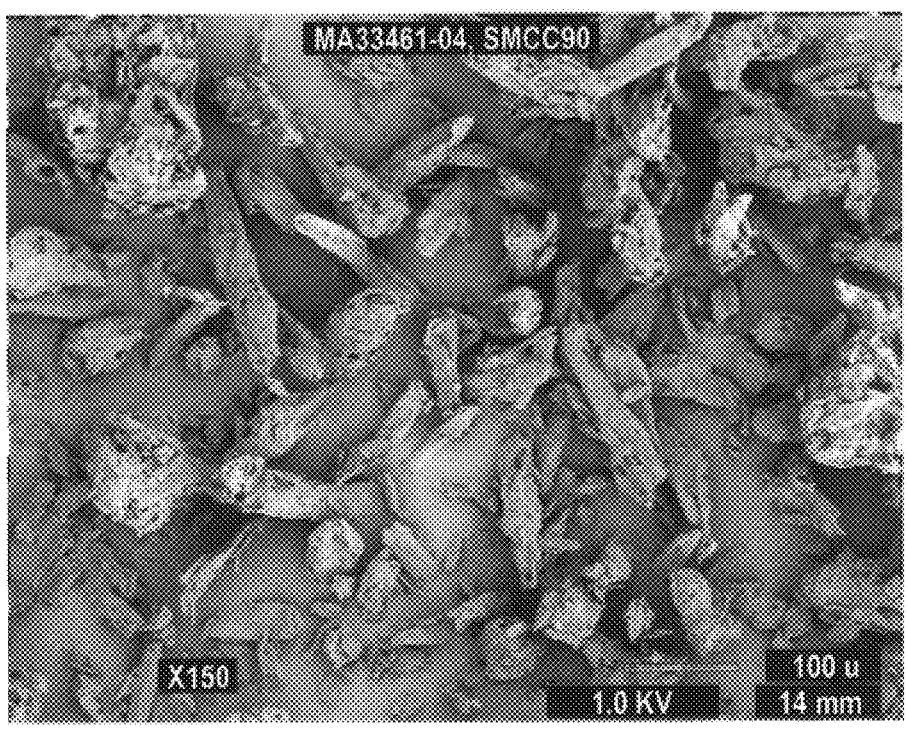
FIGS. 4A thru 4D are SEM micrographs showing the structure of silicified microcrystalline cellulose (Prosolv®90).
Figure 4B:
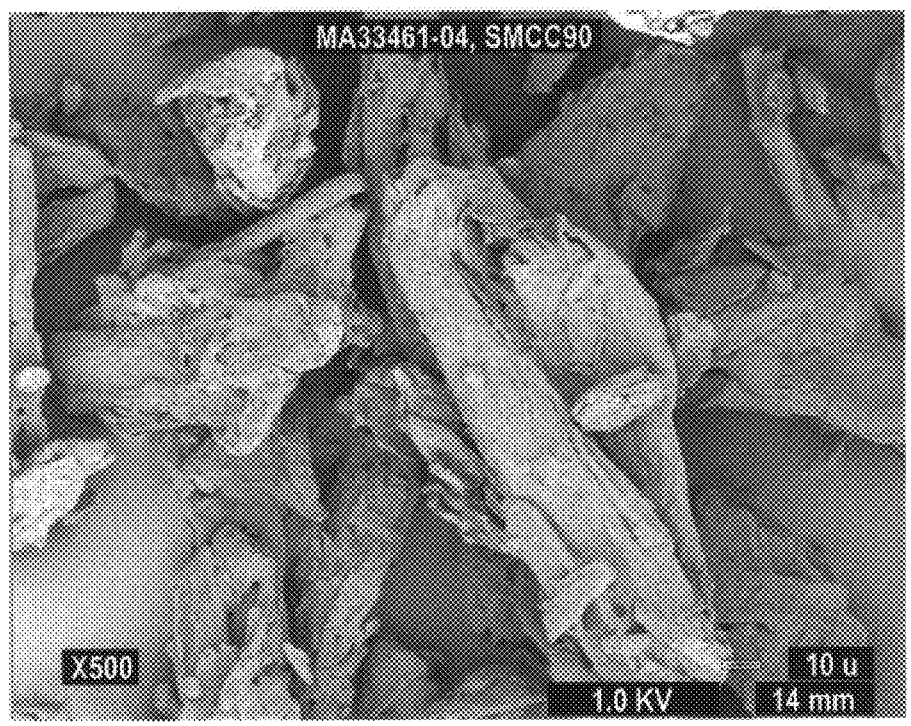
Figure 4C:
Figure 4D:
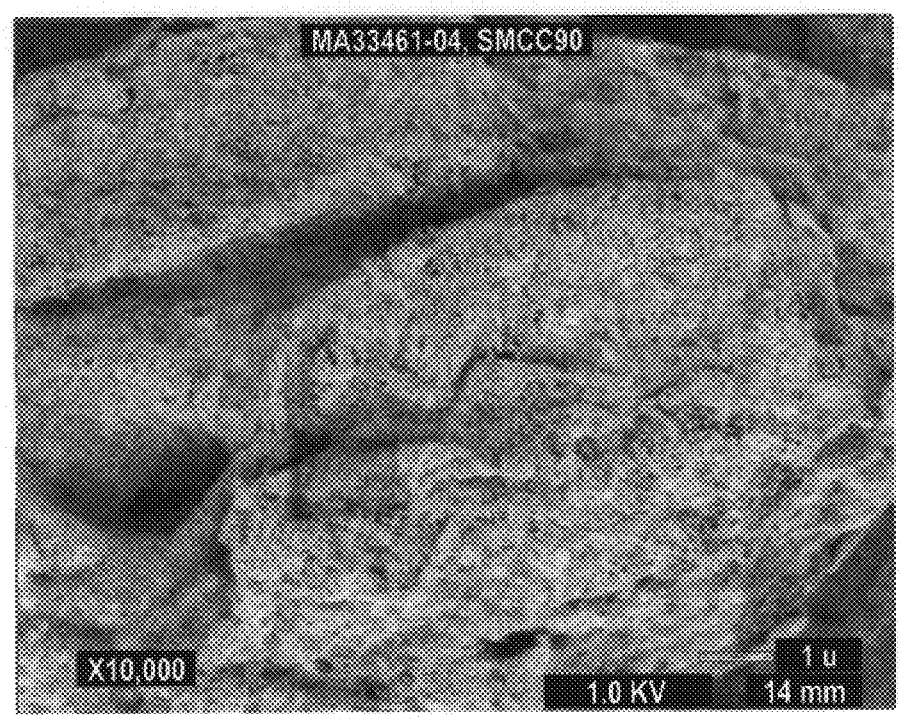
Figure 5A:
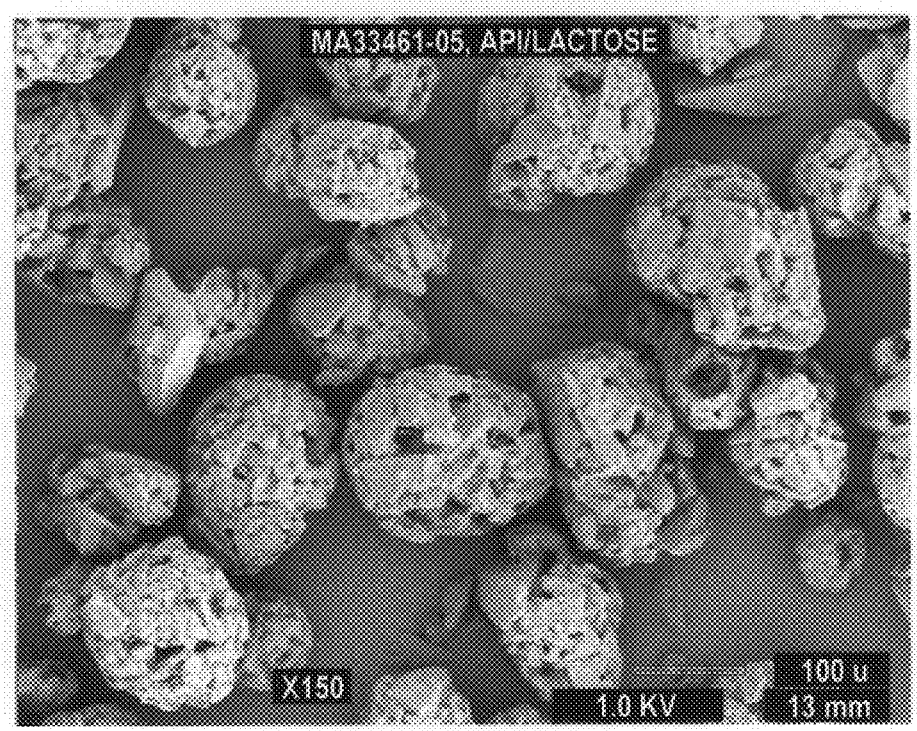
FIGS. 5A thru 5D are SEM micrographs showing the structure of a commercial levothyroxine formulation containing lactose wherein the levothyroxine is deposited on the surface of the lactose.
Figure 5B:
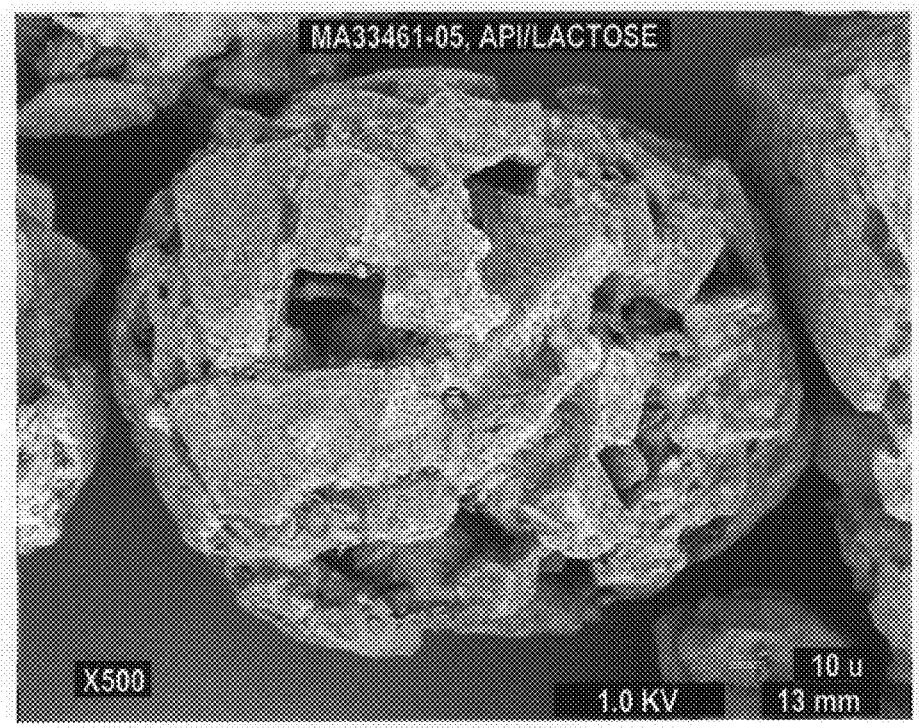
Figure 5C:
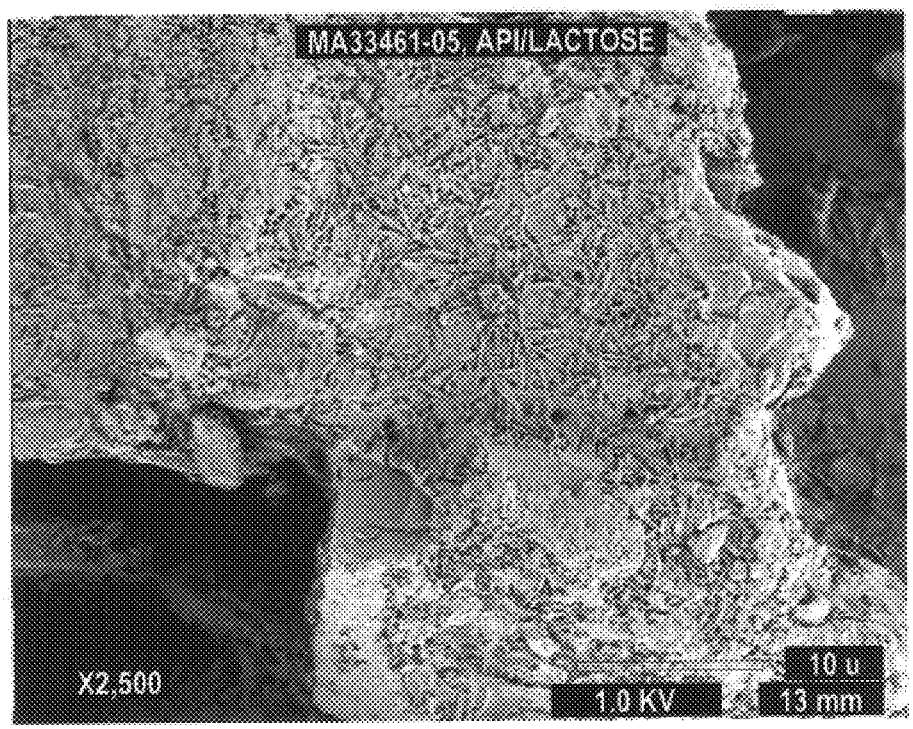
Figure 5D:
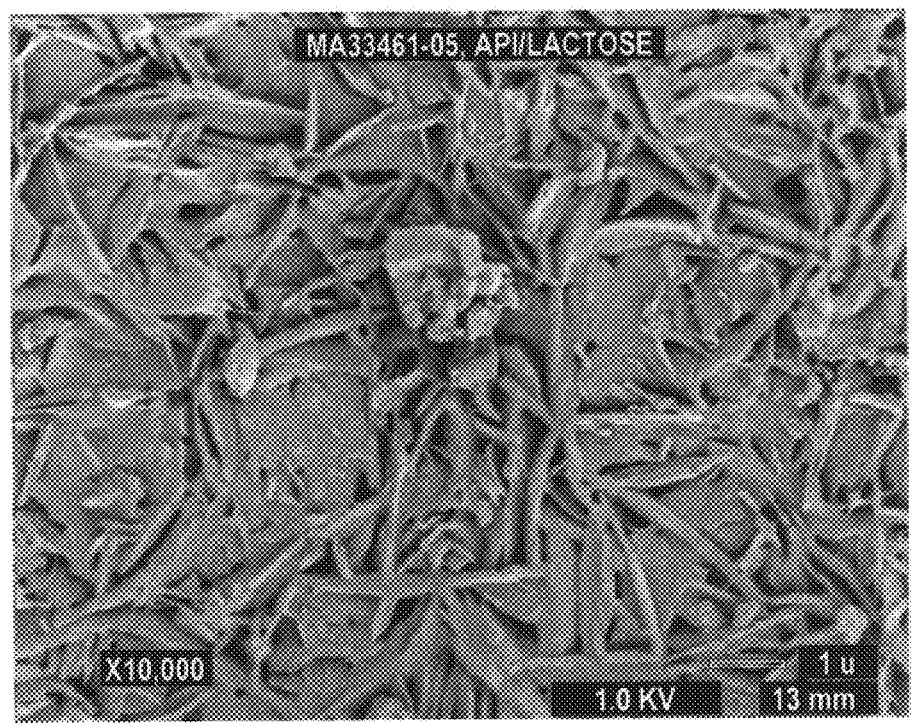
Figure 6A:
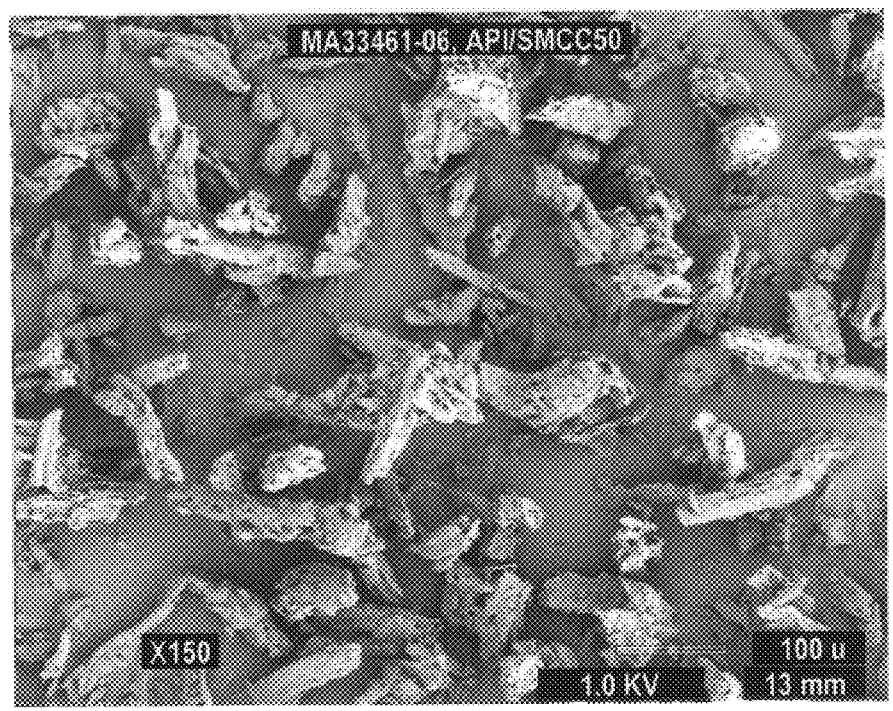
FIGS. 6A thru 6D are SEM micrographs showing the structure of a levothyroxine preparation containing silicified microcrystalline cellulose (Prosolv®50) wherein the levothyroxine is captured within the matrix of SMCC, according to the present invention.
Figure 6B:
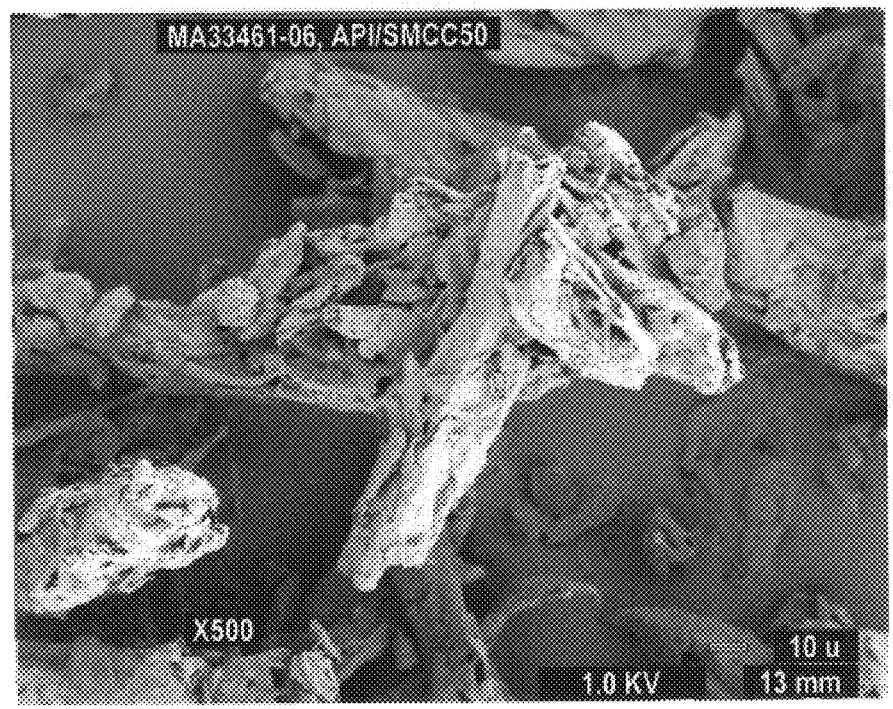
Figure 6C:
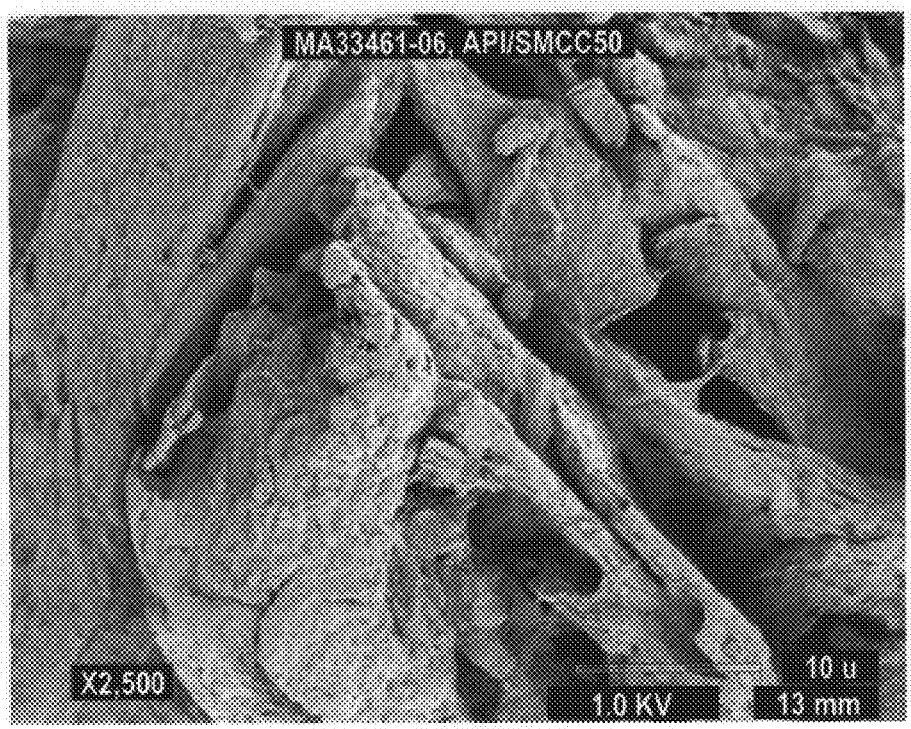
Figure 6D:
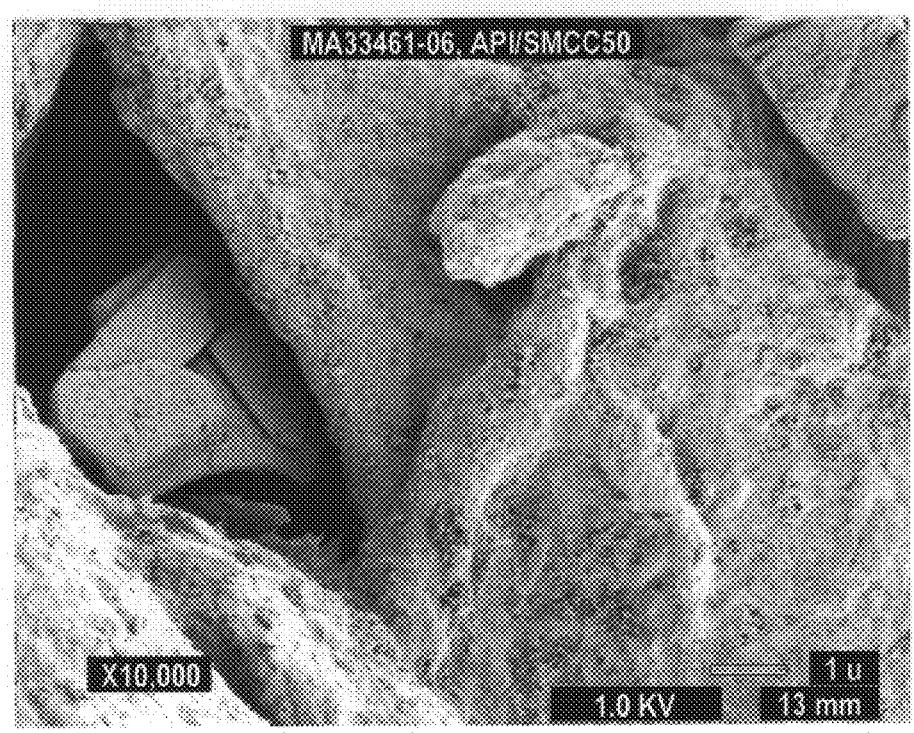
Figure 7A:
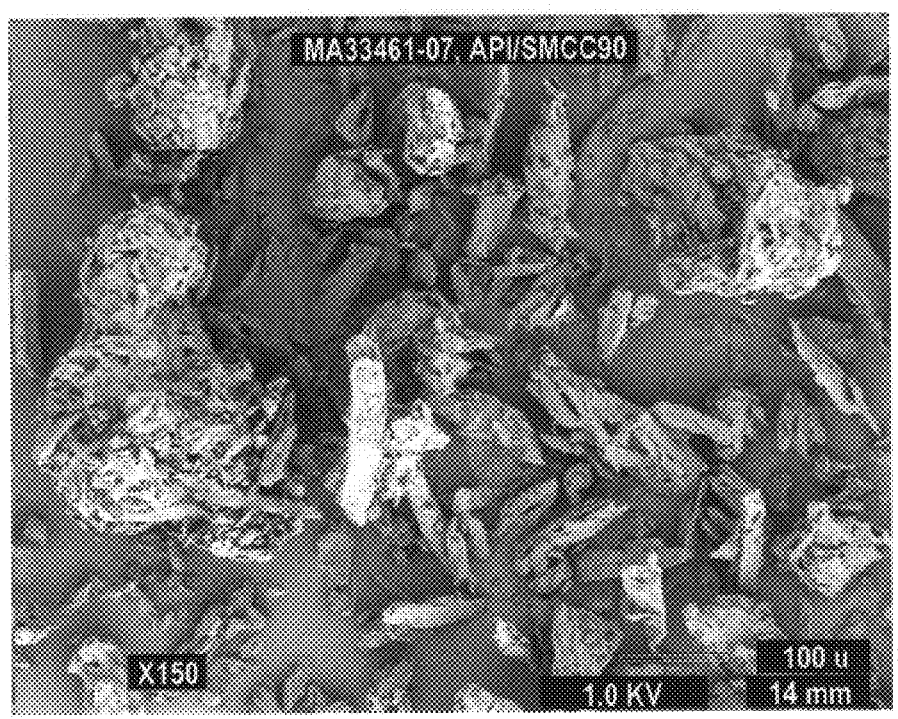
FIGS. 7A thru 7D are SEM micrographs showing the structure of a levothyroxine preparation containing silicified microcrystalline cellulose (Prosolv®90) wherein the levothyroxine is captured within the matrix of SMCC, according to the present invention.
Figure 7B:
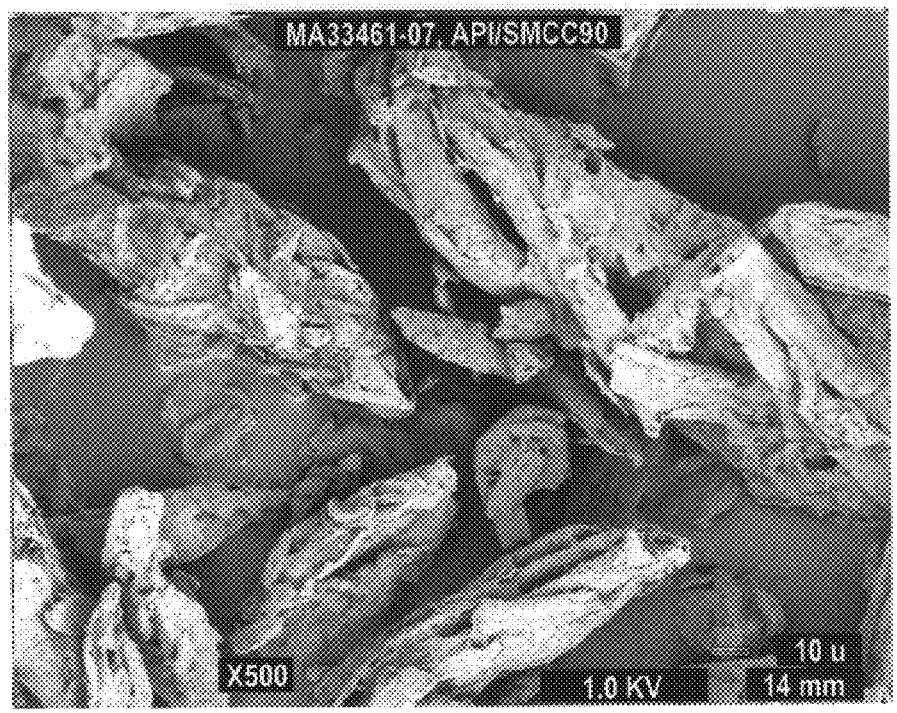
Figure 7C:
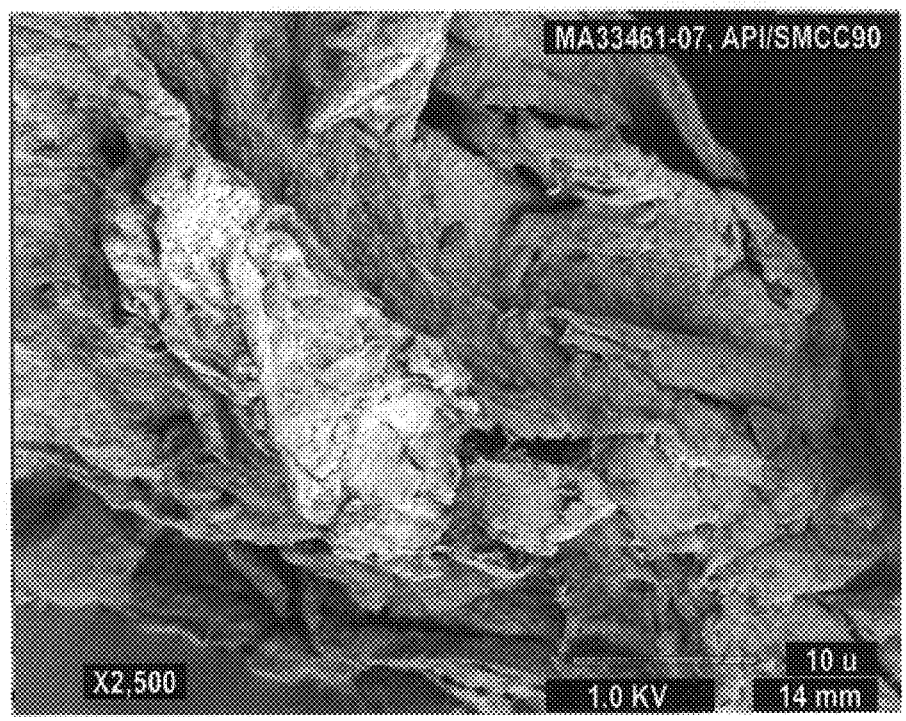
Figure 7D:
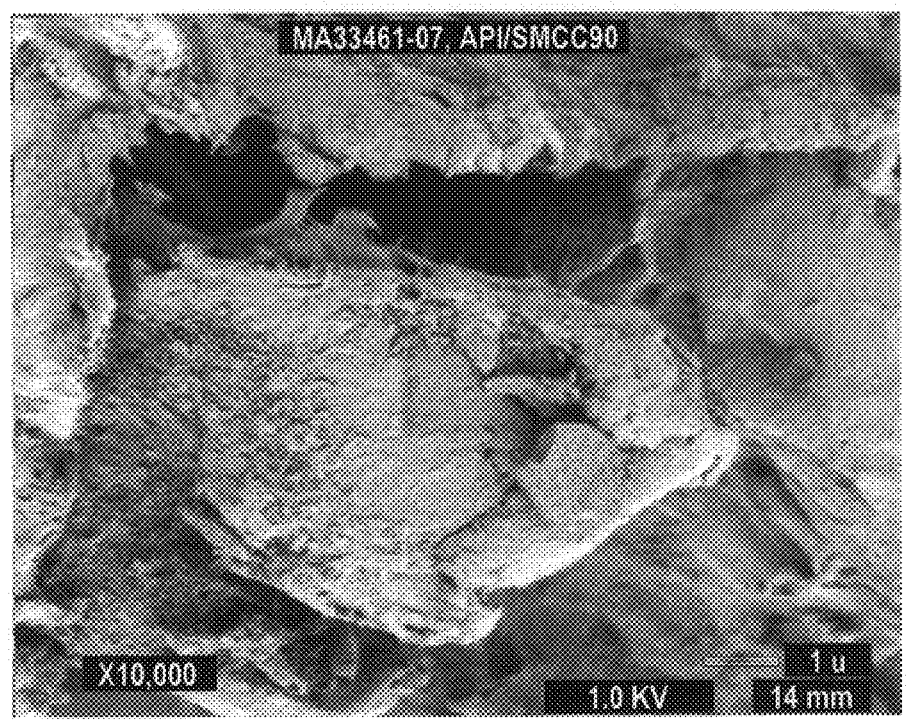

It has been surprisingly discovered that the deficiencies of the prior described pharmaceutical formulations of thyroid hormone can be overcome by the use of silicified microcrystalline cellulose as the main excipient in a tablet formulation with the thyroid hormone. Silicified microcrystalline cellulose (SMCC) is a combination of microcrystalline cellulose and colloidal silicon dioxide. Silicification of the microcrystalline cellulose is achieved by the process described in U.S. Pat. No. 5,585,115, issued to Edward H. Mendell Co., Inc.

The combination of silicified microcrystalline cellulose and thyroid hormone provides a stable, uniform pharmaceutical preparation with excellent shelf-life characteristics. While not wishing to be bound by any theory, it is believed that the silicified microcrystalline cellulose provides a stabilizing matrix for the thyroid hormone or levothyroxine sodium particles. This stabilizing matrix captures and protects the levothyroxine particles, thus providing the stabilization needed to eliminate the problems previously found with levothyroxine pharmaceutical formulations. Moreover, the silicified microcrystalline cellulose provides excellent flow characteristics, thus providing better process conditions and greater uniformity in the final formulation.

Accordingly, the novel preparations of the present invention are directed to stabilized pharmaceutical preparations comprising a therapeutically effective amount of levothyroxine sodium and silicified microcrystalline cellulose. Preferably, the stabilized pharmaceutical preparations will comprise a stabilizing matrix consisting essentially of silicified microcrystalline cellulose and a therapeutically effective amount of levothyroxine sodium particles, which levothyroxine sodium particles are captured and protected within the stabilizing matrix.

Thyroid hormones which may be used in the pharmaceutical preparations of the present invention include the following: L-3,5,3',5'-tetraiodothyronine (levothyroxine or LT4); L-3,5,3'-triiodothyronine (liothyronine or LT3); L-3,3',5'-triiodothyronine (LrT3); L-3,5-diiodothyronine (LT2); or mixtures thereof. As used herein, the term thyroid hormone should be understood to include all pharmaceutically acceptable salts thereof, preferably sodium salts.

The thyroid hormone preferably will be levothyroxine sodium and will be present in an amount sufficient to provide the desired therapeutic effect. The term "therapeutically effective amount" means the amount needed for the desired therapeutic effect and includes any additional amount or overage of active ingredient deemed necessary in the formulation to provide the desired amount upon administration.

The amounts required for a specific therapeutic purpose are known to those of skill in the art and can vary widely, based on the desired treatment. Due to the high potency exhibited by most of the thyroid hormones, the amount of active ingredient will generally be small, usually less than about 1% by weight. The minimum amount of thyroid hormone can vary, so long as an effective amount is provided to cause the desired therapeutic effect. Generally, the thyroid hormone will be present in an amount from about 0.025 mg to about 0.3 mg.

The silicified microcrystalline cellulose used in the preparation of the present invention may be any commercially available combination of microcrystalline cellulose granulated with colloidal silicon dioxide. The SMCC generally will be as described in Sherwood et al, *Pharm. Tech.*, October 1998, 78–88, and U.S. Pat. No. 5,585,115, incorporated herein by reference in its entirety. SMCC can be obtained commercially from Mendell, a Penwest Company, under the name ProSolv SMCC®. There are different grades of SMCC available, with particle size being the differentiating property among the grades. For example, ProSolv SMCC® 90 has a median particle size, by sieve analysis, in the region of 90 $\mu$m. ProSolv SMCC® 50 has a median particle size, by sieve analysis, in the region of about 40–50 $\mu$m. Generally, the particle size of the SMCC should not be larger than about 150 microns.

Since levothyroxine sodium particles have a particle size of about 2 to about 10 microns, the choice of SMCC particle size is somewhat determined by the particle differential between the SMCC and the levothyroxine. It is believed that incorporation of material with a particle distribution closer to the one of the active ingredient will result in improved uniformity. Therefore, preferably, the particle size of the SMCC will be about 50 to about 100. A combination of different grades of SMCC may be utilized.

In one embodiment, ProSolv SMCC® 90 is utilized was the SMCC. In another embodiment, ProSolv SMCC®50 is utilized as the SMCC. In a more preferred embodiment, a combination of ProSolv SMCC®50 and ProSolv SMCC®90 is used.

The amount of silicified microcrystalline cellulose used in the formulation of the present invention will be the amount necessary to stabilize levothyroxine sodium in a matrix which captures and protects the levothyroxine sodium particles. Generally, the SMCC will be present in an amount of about 50% to about 99%. Preferably, the amount of SMCC will be about 90% to about 99%.

FIGS. 1A thru 1D show the smooth crystalline structure of levothyroxine particles. This structure is important in the choice of an appropriate excipient for a stable levothyroxine pharmaceutical formulation.

FIGS. 2A thru 2D illustrate the structure of a mixture of amorphous and crystalline lactose alone and FIGS. 5A thru 5D illustrate the structure of a drug formulation of lactose and levothyroxine sodium. As shown in the SEM micrographs of FIG. 5, only surface deposition of the levothyroxine is observed.

FIGS. 3A thru 3D and 4A thru 4D depict the textured, porous surfaces of ProSolv SMCC® 50 and ProSolv SMCC® 90. Literature describes these materials as porous materials, with a surface with as much as 30% covered by pores of 2–3 microns mean diameter. FIGS. 6A thru 6D and 7A thru 7D show the formulation of the invention with levothyroxine sodium and ProSolv SMCC® 50 and levothyroxine and ProSolv SMCC® 90, respectively. As shown, the SMCC functions as a carrier and captures the levothyroxine particles within the porous matrix. Such physical interaction is believed to provide improved uniformity of the pharmaceutical product during a direct compression process. This capture within the matrix is especially important in view of the generally low amounts of active ingredient present in thyroxine hormone formulations. ProSolv SMCC® 90. Literature describes these materials as porous materials, with a surface with as much as 30% covered by pores of 2–3 microns mean diameter. FIGS. 6 and 7 show the formulation of the invention with levothyroxine sodium and ProSolv SMCC® 50 and levothyroxine and ProSolv SMCC® 90, respectively. As shown, the SMCC functions as a carrier and captures the levothyroxine particles within the porous matrix. Such physical interaction is believed to provide improved uniformity of the pharmaceutical product during a direct compression process. This capture within the matrix is especially important in view of the generally low amounts of active ingredient present in thyroxine hormone formulations.

The formulation of the present invention may include a number of other ingredients for optimal characteristics of the pharmaceutical composition. Such other ingredients and the amounts to be used are within skill of the art and are known in the pharmaceutical art. These may include disintegrants, lubricants and/or coloring agents, among others. Suitable disintegrants include, for example, sodium starch glycolate, other starches such as pregelatinized starch, and celluloses. Suitable lubricants may be provided such as magnesium stearate, calcium stearate, talc and stearic acid. Any coloring agent certified by the FDA may be used, such as FD&C Yellow #6, among others.

Figure 8:
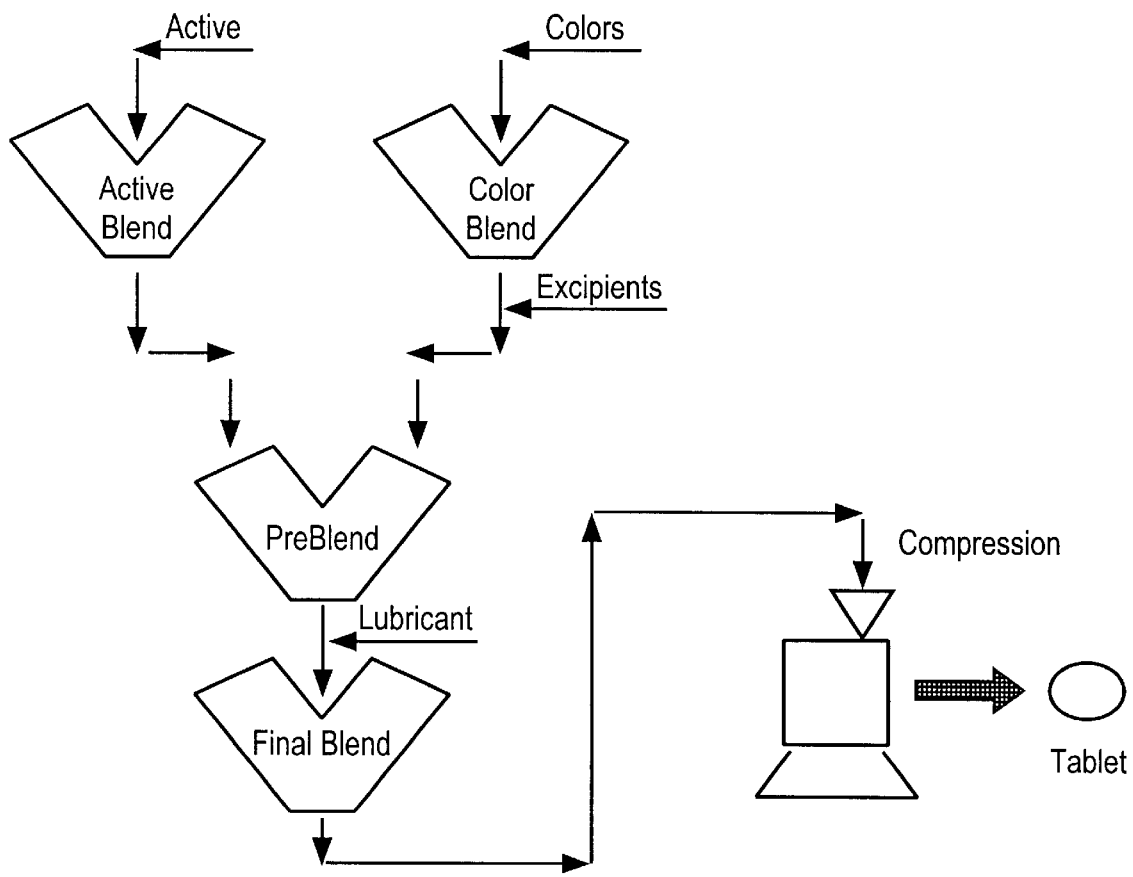
FIG. 8 is a flow diagram illustrating an embodiment of a direct compression process according to the present invention for the production of the thyroid hormone preparation of the present invention.

The pharmaceutical preparation of the present invention may be prepared using a direct compression method, a dry granulation method or by wet granulation. Preferably, the thyroid hormone preparation of the present invention will be prepared using a direct compression process. This preferred process consists of two main steps: blending and compression. FIG. 8 illustrates the general process of the invention. The blending step is composed of an active blend, color blend, pre-blend, and final blend (lubrication).

In one embodiment, the present invention provides a method for the manufacture of a pharmaceutical tablet preparation comprising the steps of: (a) forming an active blend by blending in intimate admixture silicified microcrystalline cellulose and a therapeutic agent comprising one or more thyroid hormone or hormones; (b) forming a color blend by blending in intimate admixture one or more pharmaceutically acceptable dyes and silicified microcrystalline cellulose; (c) combining the active blend, the color blend and a disintegrant in a preblend; (d) adding a lubricant to the preblend to form a final blend; and (e) compressing the final blend to form a pharmaceutical tablet preparation.

This process has been found to be reproducible and strength independent. The operation of the blending equipment and settings for carrying out the process of the invention will be understood to anyone of skill in the art. Likewise, the compression of the pharmaceutical preparation of the present invention can be carried out by any of the known methods and with equipment and settings which would be known to one of skill in the art.

A screening step may be introduced between the active blend and preblend portions of the blending step to prevent agglomerates of active particles (>250 microns in size) to be carried over to the preblend portion. For example, a screen #60, which contains open surface areas of 250 microns, may be used. Other methods and equipment utilized for screening particles will be known to those of skill in the art. The flow properties of the mixture are not affected by incorporation of the silicified microcrystalline cellulose in the active blend and the screening step.

The thyroid hormone tablets resulting from the direct compression process of the present invention exhibit the stability and uniformity required for such formulations.

The invention will now be more fully explained by the following examples. However, the scope of the invention is not intended to be limited to these examples.

EXAMPLES

Example 1

A preparation according to the present invention was prepared with the following ingredients (Lot #1355-006-039):

| Ingredients | Function | mg/tablet | % w/w |
|---|---|---|---|
| Levothyroxine, U.S.P. | Active | 0.025 | 0.02 |
| Prosolv SMCC ™ 90 | Diluent | 115.84 | 94.18 |
| Sodium Starch Glycolate, NF | Disintegrant | 6.15 | 5.00 |
| Magnesium Stearate, NF | Lubricant | 0.861 | 0.70 |
| FD & C Yellow #6 | Coloring Agent | 0.123 | 0.10 |
| | | 123 mg | 100% |

1355-006-039: Initial (T0) assay 98.1%

The stability results for lot 1355-006-039 at ACC/40° C.:75%R.H. are given below.
1355-006-039:

| | % Assay/month | | |
|---|---|---|---|
| | T1 | T2 | T3 |
| $t_0$ = 98.1% | 94.5 | 94.4 | 93.3 |

Figure 9:
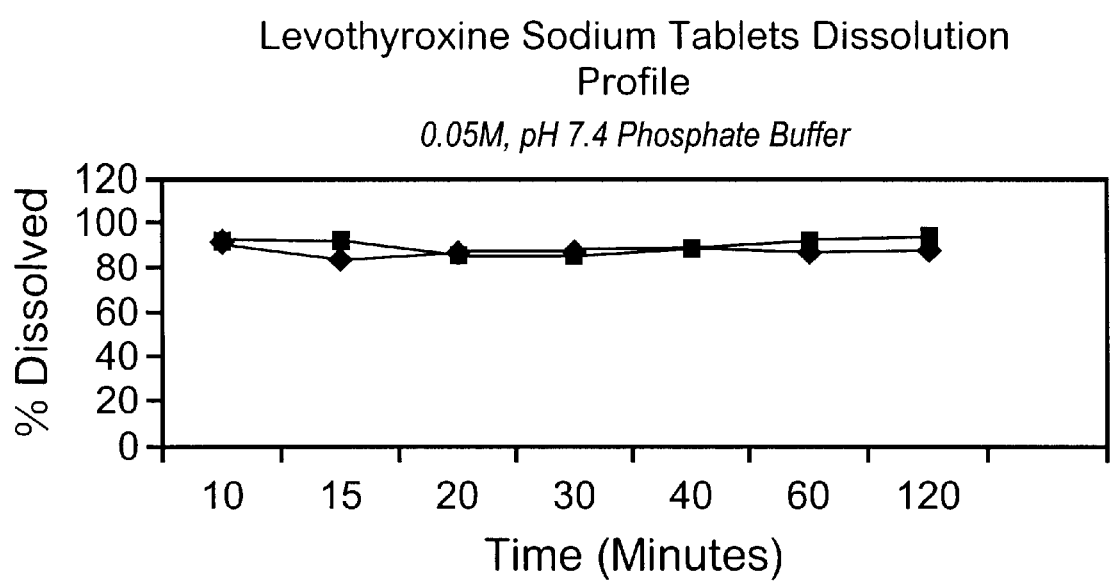
FIG. 9 is a graph showing the dissolution profile of the levothyroxine sodium preparation according to the present invention described in Example 1.

The results show excellent initial assay and stability. For this formulation, an approximately 5% initial assay drop was observed after three months accelerated stability. This stability behavior represents an improvement over the lactose-based formula, where an 18% drop is observed under the same conditions. The dissolution profile met U.S.P. requirements as shown in FIG. 9.

Example 2

Three lots (containing 2% active overage) were manufactured at commercial scale, containing Prosolv™ 50 (9.3% w/w final blend) and Prosolv™ 90 (84.8% w/w final blend). The results of the final blend showed an average percent assay of 99.2% and an RSD of 0.9%. Content uniformity for 30 tablets was found to be 102.1% with an RSD of 4.2%. The ingredients of the three lots were as follows:

| 0.025 mg strength | | | |
|---|---|---|---|
| Ingredients | Function | mg/tablet | % w/w |
| Levothyroxine, U.S.P. | Active | 0.025 | 0.021 |
| Prosolv SMCC ™ 50 | Diluent | 11.429 | 9.29 |

-continued

| 0.025 mg strength | | | |
|---|---|---|---|
| Ingredients | Function | mg/tablet | % w/w |
| Prosolv SMCC ™ 90 | Diluent | 104.28 | 84.77 |
| Sodium Starch Glycolate, NF | Disintegrant | 6.143 | 4.99 |
| Magnesium Stearate, NF | Lubricant | 0.857 | 0.70 |
| FD & C Yellow #6 | Coloring Agent | 0.277 | 0.22 |

Each of the three lots was prepared according to FIG. 8 which is a flow chart illustrating the direct compression process utilized. The active blend comprises ProSolv50® and levothyroxine which was blended in a blender. A portion of the ProSolv 90® and the color was blended in a blender to form the color blend. For two of the lots, the active blend was then screened in a #60 mesh screen before passing to the preblend step. The rest of the ProSolv 90™ excipient was added to the color blend, which was then added to the preblend step. The preblend was mixed in a blender and included the active ingredient, the color blend and sodium starch glycolate. The lubricant magnesium stearate was added after the preblend step and prior to the final blend step. After the final blend, the material was then subjected to tablet compression via direct compression using a Courtoy tablet compression machine.

The stability of the product is shown in the table below:

| Storage Condition | A | B | C |
|---|---|---|---|
| Initial $T_0$ | 99.3% | 101.0% | 101.8% |
| RT | | | |
| 1 month | 99.8% | 99.3% | ND |
| 2 months | 104.2% | 100.0% | ND |
| 3 months | 95.6% | 100.3% | ND |
| 6 months | 94.4% | 96.6% | ND |
| INT | | | |
| 1 month | 98.4% | 98.8% | ND |
| 2 months | 101.7% | 100.8% | ND |
| 3 months | 96.4% | 93.8% | ND |
| 6 months | 94.4% | 96.4% | ND |
| ACC | | | |
| 1 month | 95.6% | 98.1% | 94.1% |
| 2 months | 95.6% | 96.2% | 94.4% |
| 3 months | 90.6% | 91.7% | 90.3% |

RT: 25 ± 2° C., 60% R.H.
INT: 30 ± 2° C., 60% R.H.
ACC: 40 ± 2° C., 75% R.H.
ND: Not Determined While the invention has been described with preferred embodiments, it is to be understood that variations and modifications may be resorted to as will be apparent to those skilled in the art. Such variations and modifications are to be considered within the purview and the scope of the claims appended hereto.

We claim:
1. A stabilized pharmaceutical preparation comprising a therapeutically effective amount of levothyroxine sodium and silicified microcrystalline cellulose.
2. The preparation of claim 1, further comprising a disintegrant and a lubricant.
3. The preparation of claim 2, wherein the disintegrant is sodium starch glycolate.
4. The preparation of claim 2, wherein the lubricant is magnesium stearate.

5. A stabilized pharmaceutical preparation comprising a stabilizing matrix consisting essentially of silicified microcrystalline cellulose and a therapeutically effective amount of levothyroxine sodium particles, which particles are captured and protected within the stabilizing matrix.

6. The preparation of claim 5, further comprising a disintegrant, a lubricant and a coloring agent.

7. The preparation of claim 6, wherein the disintegrant is sodium starch glycolate, pregelatinized starch or cellulose.

8. The preparation of claim 6, wherein the lubricant is magnesium stearate, calcium stearate, talc or stearic acid.

9. The preparation of claim 6, wherein the disintegrant is sodium starch glycolate and the lubricant is magnesium stearate.

10. The preparation of claim 1, wherein the stabilized pharmaceutical preparation is in the form of a tablet.

11. A stabilized pharmaceutical preparation comprising a therapeutically effective amount of a thyroid hormone and silicified microcrystalline cellulose.

12. A method for the manufacture of a pharmaceutical tablet preparation comprising the steps of:

(a) forming an active blend by blending in intimate admixture silicified microcrystalline cellulose and a therapeutic agent comprising one or more thyroid hormone or hormones;

(b) forming a color blend by blending in intimate admixture one or more pharmaceutically acceptable dyes and silicified microcrystalline cellulose;

(c) combining the active blend, the color blend and a disintegrate in a preblend;

(d) adding a lubricant to the preblend to form a final blend; and (e) compressing the final blend to form a stabilized pharmaceutical tablet preparation.

13. The method of claim 12, wherein the thyroid hormone is levothyroxine sodium.

14. The method of claim 13, wherein the disintegrant is sodium starch glycolate.

15. The method of claim 13, wherein the lubricant is magnesium stearate.

* * * * *